United States Patent [19]

Gansow et al.

[11] Patent Number: 4,831,175

[45] Date of Patent: May 16, 1989

[54] BACKBONE POLYSUBSTITUTED CHELATES FOR FORMING A METAL CHELATE-PROTEIN CONJUGATE

[75] Inventors: Otto A. Gansow, Washington, D.C.; Martin W. Brechbiel, Falls Church, Va.

[73] Assignee: The United States of America as represented by the Secretary of the Department of Health and Human Services, Washington, D.C.

[21] Appl. No.: 903,723

[22] Filed: Sep. 5, 1986

[51] Int. Cl.$^4$ .................... C07C 161/04; C07C 79/46; C07C 101/42; C07D 207/46
[52] U.S. Cl. ..................................... 558/17; 562/437; 562/443; 548/542
[58] Field of Search ................. 558/17; 562/449, 437, 562/443; 560/41; 548/546, 542

[56] References Cited

FOREIGN PATENT DOCUMENTS 2109407 6/1983 United Kingdom ................. 558/17

OTHER PUBLICATIONS

Chang et al., "Bifunctional Chelating Agents: Linking Radiometals to Biological Molecules", *Applications of Nuclear and Radiochemistry*, pp. 103-114.
McOmie, Protective Groups in Organic Chemistry, 1973, Plenum Press, New York, pp. 44 & 45.

*Primary Examiner*—Mary C. Lee
*Assistant Examiner*—Robert C. Whittenbaugh
*Attorney, Agent, or Firm*—Holman & Stern

[57] ABSTRACT

New polysubstituted diethylenetriaminepentaacetic acid chelates and protein conjugates of the same are described together with the methods of preparing such compounds. A method of delivering radiolabelled compound of the present invention to a target site while minimizing the distribution of the compound to non-targeted organs or tissues is also disclosed.

8 Claims, 2 Drawing Sheets

BACKBONE POLYSUBSTITUTED CHELATES FOR FORMING A METAL CHELATE-PROTEIN CONJUGATE

BACKGROUND OF THE INVENTION

This invention relates to metal chelates and the formation of metal-chelate protein conjugates.

Interest in the art in metal chelates and in methods for forming metal chelate-protein conjugates for diagnostic and therapeutic purposes continues. Representative type chelates and conjugates and methods for forming conjugates are disclosed, inter alia, in U.S. Pat. Nos. 4,454,106, 4,472,509, 4,339,426. One example of such conjugates is a metal chelate-monoclonal antibody conjugate. Other proteins including antibody fragments, polyclonal antibodies, antigens, blood proteins, or proteins bound to blood lymphocytes or other cells can also be employed in the formation of conjugates.

A method for synthesis of bifunctional metal chelates for conjugation to proteins involves reduction of amino acid amides to ethylenediamines to form monosubstituted derivatives which are converted to bifunctional ethylenediaminetetraacetic acid (EDTA) chelates by alkylation with haloacetic acid. (Yeh, et al. 100 Anal. Biochem. 152,1979). Similarly, monosubstituted diethylenetriamine is synthesized by reaction of ethylenediamine with an amino acid ester and reduction of the resulting amide carbonyl. (Brechbiel, et al. 25 Inorg. Chem. 25: 2772-2781 (1986). Alkylation of the diethylenetriamine with haloacetic acid produces a monosubstituted bifunctional diethylenetriaminepentaacetic acid (DTPA) chelate.

Another method of synthesis of a bifunctional DTPA involves reaction of a DTPA or EDTA carboxylate with an chloroformate ester to form a reactive anhydride. (Krejcarek, et al. 77 Biochem. Biophys. Res. Commun. 581, 1977). The dianhydride of DTPA used as a bifunctional chelate is prepared by dehydration of the parent DTPA. (Hnatowich, et al. 33 Int. J. Appl. Rad. Isot. 327, 1982). The practice of using an EDTA chelate monosubstituted at the carbon-1 position to better retard the release of metal from chelate in vitro than the unsubstituted EDTA chelate has also been reported. (Meares, et. al. 142 Anal. Biochem. 68, 1984).

Generally, the prior art has formed metal-protein chelate conjugates by mixing monosubstituted bifunctional EDTA or DTPA chelates or DTPA anhydrides with proteins followed by reaction with the metal to be chelated. (Krejcarek, et al., 77 Biochem. Biophys. Res. Commun. 581, 1977); Brechbiel, et al. 25 Inorg. Chem. 5783, 1986). Imaging of tumor target sites in vivo with metal chelate conjugated monoclonal antibodies prepared according to these methods has been reported. (Khaw, et al. 209 Science 295, 1980). Sheinberg, et al. 215 Science 1511, 1982). Diagnosis of human cancer in vivo using metal chelate conjugated monoclonal antibody has also been reported. (Rainsbury, et al. Lancet 2, 694, 1983). But attempts to employ the tumor localizing properties of metal chelate conjugated monoclonal antibodies for therapeutic purposes have not found common usage, in part because metals may be (and often are) released from the metal chelate conjugate in vivo and, particularly in the case of radioactive metal salts, may produce undesirable concentrations of toxic radionuclides in bone marrow or the like even if the conjugates are rigorously purged of adventitiously bonded metal. A process for purifying metal chelate protein conjugates of adventitiously bonded metals is disclosed in U.S. Pat. No. 4,472,509. The importance of using very strong metal chelates to firmly link radiometals to monoclonal antibodies and of rigorous purification of the conjugates to effect maximal tumor localization and minimize delivery to non-target tissues is discussed in Brechbiel, et al. (25 Inorg. Chem. 1986). Undesirable localization of potentially therapeutic radionuclides released in mice in vivo from metal chelate conjugated polyclonal antibodies have precluded therapy investigation in humans. (Vaughn, et. al. EIR-Bericht. 78, 1986). Increased in vivo bone uptake of radiometal injected for therapy as a metal chelate conjugated monoclonal antibody has also been reported. (Hnatowich, et al. 26 J. Nucl. Med. 503, 1985). The amount of potentially therapeutic doses in humans of radiometal chelated polyclonal antibody has been limited by bone marrow toxicity (Order, et al, 12 Int. J. Rad. Oncol. 277, 1986).

It is evident from the above that there continues to be a need for more effective metal chelate protein conjugates that firmly link metals to proteins to minimize metal release and permit highly selective delivery of metals to targeted sites in vivo.

SUMMARY OF THE INVENTION

It is, therefore, an object of the present invention to provide novel polysubstituted diethylenetriamines.

It is another object of the present invention to provide novel polysubstituted bifunctional diethylenetriaminepentaacetic acid chelates.

It is yet another object of this invention to provide novel chelate-protein conjugates.

It is a still further object of this invention to provide novel metal chelate protein conjugates.

Other objects and advantages of the present invention will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings for preparation of compounds of Formula 1, wherein.

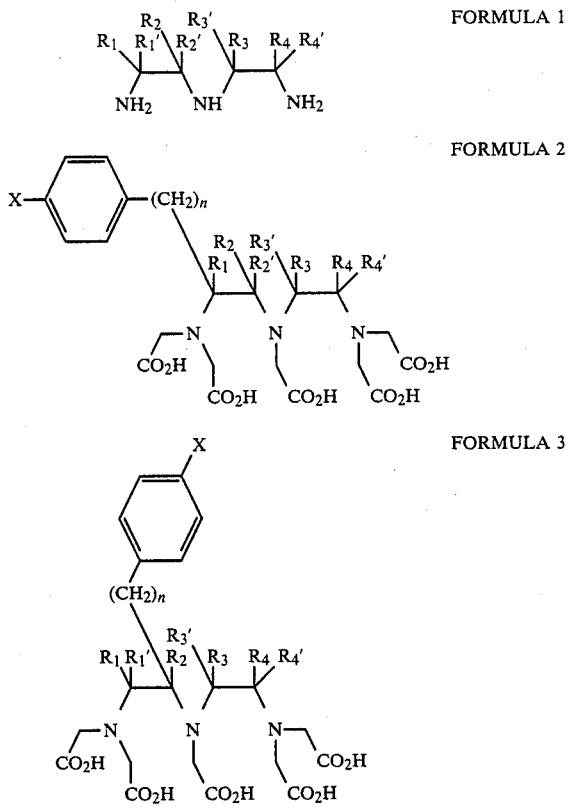

FORMULA 1

FORMULA 2

FORMULA 3

DETAILED DESCRIPTION OF INVENTION

Figure 1:
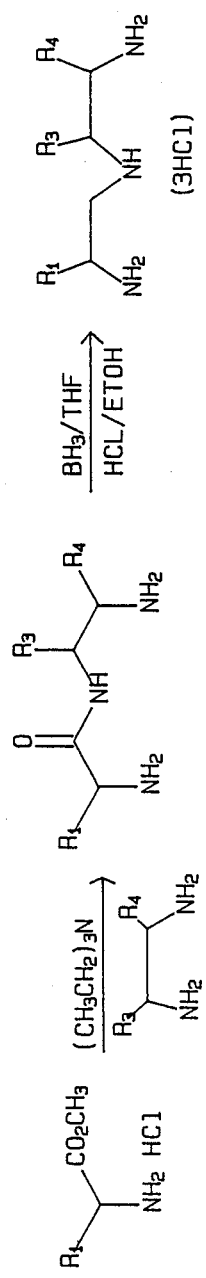
FIG. 1 shows a scheme for preparation of a polysubstituted diethylenetriamine, where $R_1$ is para-nitrobenzyl and $R_{3,4}$ are aryl/alkyl groups as described in the text. In the case where $R_{3,4}$ are the methyl group, the diethylenetriamine product of the scheme is compound (d) of Table 1.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

An aspect of this invention contemplates the synthesis of diethylenetriamines in which the carbon backbone is polysubstituted but contains at least two substituents. This synthesis is performed by carbodiimide coupling of appropriately substituted alpha amino acid amides with substituted amino acids followed by reduction of the resulting amide to the triamine.

Another aspect of the invention contemplates the condensation of an appropriately substituted alpha amino acid with a substituted alpha amino oxime followed by reduction to the desired triamine.

A further aspect of this invention contemplates a particularly useful series of bifunctional chelates comprising diethylenetriaminepentaacetic acid substituted on the carbon backbone by at least two side chains (polysubstituted), one of which contains a nitro substituent. These chelates may be prepared by haloacid alkylation of appropriately polysubstituted diethylenetriamines.

In another aspect, the invention contemplates a series of diethylenetriaminepentaacetic acid chelates substituted on the carbon backbone by at least two substituents with one side chain containing a nitro, amino or an isothiocyanate or an N-hydroxysuccinimide ester substituent.

In yet another aspect, this invention contemplates protein conjugates of a series of diethylenetriamine pentaacetic acid chelates substituted on the carbon backbone by at least two substituents.

Yet another aspect of this invention contemplates metal chelate conjugated proteins formed by conjugation to protein of a series of diethylenetriaminepentaacetic acid chelates or metal chelates substituted on the carbon backbone by at least two substituents which are not H.

More particularly, the present invention provides metal chelate conjugated proteins, especially metal chelate conjugated monoclonal antibodies or antibody fragments, which retain their biological activity and specificity, are substantially free of adventitously bonded metals, and which in vivo retain the metal tied to the protein better than the conjugates known in the prior art. Metals which are released in vivo can be bound by transferrin, metallothionen or other metal binding proteins (e.g. ferritin) which are present in the blood. Such metals are retained in the circulatory system often for long periods of time and are cleared to various organs of the reticuloendothelial system (RES), to the bone, bone marrow or to kidney. Such clearance results in a concentration of the metal in the liver, spleen, kidney, bone or bone marrow. It is apparent that random, long term circulation of radiometals or concentration of radioactive materials in non-targeted organs such as liver, spleen, bone, bone marrow or kidney are highly undesirable. It is an object of the present invention to alleviate such serious problems.

A large number of bifunctional chelates which have been indicated to be useful in conjugating metals, especially radiometals, to proteins are not sufficiently strong to adequately retain metals in vivo for use in diagnosis. Thus bifunctional EDTA complexes of Indium de-metallate in a mouse model, as do anhydride linked DTPA complexes of Indium (Brechbiel, et al. 25 Inorg. Chem. 1986).

Prior art DTPA-containing protein conjugates have coupled the DTPA through a carboxylate group of the DTPA or through a functional group on a side chain attached to a nitrogen of the DTPA. These chelates are not as stable as the backbone polysubstituted chelates of the present invention. A backbone monosubstituted DTPA has also been coupled to proteins but yttrium and bismuth complexes of that chelate are not as stable as those of the chelates of the present invention.

Preferred embodiments and a detailed explanation of the invention are provided in the following description, and utility further delineated by the accompanying examples.

PREFERRED EMBODIMENTS OF THE INVENTION

In accordance with the present invention, the bifunctional chelate has, as one portion of its structure, a side chain linked to a carbon atom of the chelate backbone which serves to sterically hinder the conformational opening of the chelate structure required for release of a metal from the chelate. Any of a variety of side chains may be employed, the choice being within one of ordinary skill in the art. The side chain may contain carbon to carbon or ether, linkages or the like. Hydrocarbon side chains are preferred. If there are heteroatoms present, for example in ether linkages, they may be counted as carbon atoms for the purpose of chain length determinations. Such structures include, without limitation, straight or branched chain alkyl groups having 1 to about 15 carbon atoms such as methylene, ethylene, propylene, butylene, isopropylene and the like; a straight or branch chain alkene group having 1 to about 15 carbon atoms including ethene, propene, butene and the like and isomers thereof; aryl groups including phenyl, diphenyl, napthyl and the like; and alkyl aryl groups having 1 to about 15 carbon atoms in one or more branched or straight chain alkyl groups, including benzyl, phenyl ethylene, phenyl propylene and the like. The side chain should be essentially free of reactive groups, especially those easily reduced by hydrogen and hydride reagents. Preferred side chains include straight or branched chain alkanes with 5 or less carbons, benzyl, and phenylethylene. A most preferred such side chain is the methyl group as denoted in Table 2 and Formula 2, 3.

The bifunctional chelates of this invention have in another portion of their molecular structure a substituent with a reactive functional group attached to a carbon atom of the chelate backbone and which reacts directly with amino acid residues of a protein to form a covalent linkage. Such reactive functional groups include isothiocyanate, the N-hydroxysuccinimide ester and haloacetamide. The reactive functional group, according to the practice of this invention, may be attached directly to the chelate backbone or may be attached through a wide variety of side chains. Any of a wide variety of side chains may be employed and the choice of a particular one will be within the skill of the art. Hydrocarbon side chains are preferred. If there are heteroatoms present, for example in ether linkages, interrupting the carbon backbone, they may be counted as carbon atoms for the purpose of chain length determinations. Such structures include, without limitation, straight or branch chain alkyl groups having 1 to about 15 carbon atoms such as methylene, ethylene, propylene, butylene, isopropylene and the like; a straight or branch chain alkene group having 1 to about 15 carbon atoms including ethene, propene, butene and the like and isomers thereof; aryl groups including phenyl, diphenyl, napthyl and the like; and alkyl aryl groups having 1 to about 15 carbon atoms in one or more branched or straight chain alkyl groups, including benzyl, phenyl ethylene, phenyl propylene and the like. The essential purpose of this side chain is only to serve as a stable link between the chelate and the functional group. The side chain should be essentially free of reactive groups other than the desired functional groups as described above. Preferred side chains include substituted straight chain alkanes, benzyl, and phenylethylene.

In a preferred aspect of this invention, diethylenetriamines of the structure shown in formula (1), with the substituents of Table 1 as intermediates in the preparation of the polysubstituted DTPA derivatives of Formulas 2, 3 are desired.

Prefered chelates are represented in Formula 2.

In formula (2), X is preferably haloacetamide, isothiocyanate or N-hydroxysuccinimide and $R_1$-$R_4$, $R_1'$-$R_4'$ are H, or alkyl groups with 5 or less carbon atoms, irrespective of isomeric structure or permutation and $n \leq 5$.

In another preferred aspect of this invention, chelates of the structure shown in formula 3 are desired, where X, $R_1$-$R_4$, $R_1'$-$R_4'$ and n are the same as in formula 2.

Most preferred for the practice of this invention are the compounds of formula 2 and 3 wherein the substituents are as shown in Table 2 and referred to as compounds 2(a), 2(b), 3(c) and 2(d).

TABLE 1

The following substituents refer to Formula 1.

| | $R_1$, $R_1'$ | $R_2$, $R_2'$ | $R_3$, $R_3'$ | $R_4$, $R_4'$ |
|---|---|---|---|---|
| 1 (a) | SCNBz, H | H, H | $CH_3$, H | H, H |
| 1 (b) | SCNBz, H | H, H | H, H | $CH_3$, H |
| 1 (c) | H, H | SCNBz, H | H, H | $CH_3$, H |
| 1 (d) | SCNBz, H | H, H | $CH_3$, H | $CH_3$, H | wherein SCNBz is para-isothiocyanatobenzyl

TABLE 2

The following substituents refer to Formula 2 or 3.

| | $R_1$, $R_1'$ | $R_2$, $R_2'$ | $R_3$, $R_3'$ | $R_4$, $R_4'$ |
|---|---|---|---|---|
| 2 (a) | SCNBz, H | H, H | $CH_3$, H | H, H |
| 2 (b) | SCNBz, H | H, H | H, H | $CH_3$, H |
| 3 (c) | H, H | SCNBz, H | H, H | $CH_3$, H |
| 2 (d) | SCNBz, H | H, H | $CH_3$, H | $CH_3$, H | wherein SCNBz is para-isothiocyanatobenzyl

The introduction of reactive side chains into the carbon backbone structure of chelates has been described in the prior art. (Meares, et. al. 142 Anal. Biochem. 68, 1984).

Essentially all syntheses of DTPA have as their penultimate reaction step the alkylation of a parent diethylenetriamine. Thus the methods for preparation of carbon backbone polysubstituted DTPA reduces to the preparation of the parent diethylenetriamines.

The conventional method for preparation of a substituted diethylenetriamine is illustrated in FIG. 1. The process consists of reaction of an amino acid ester with an ethylenediamine followed by reduction to the diethylenetriamine.

The reactions of FIG. 1 can be used to provide a novel compound 1(d) of Table 1 wherein $R_1$ is para-nitrobenzyl and $R_3$, $R_4$ are methyl. In accordance with this scheme, 2,3-diaminobutane may be reacted with p-nitrobenzylalanine methyl ester and the product reduced with diborane to provide the parent diethylenetriamine of 2(d). To produce 2(d), the nitrogens of the parent diethylenetriamine are alkylated with bromoacetic acid, the nitro group is then catalytically reduced with hydrogen, and the resulting amine reacted with thiophosgene.

However, if the method of FIG. 1 is used to prepare the compounds 2(a) and/or 2(b) of the Table 2, the result of the reaction of 1,2-diaminopropane with p-nitrophenylalanine methyl ester, followed by reduction, alkylation, reduction and thiocarbonylation steps of the paragraph above, results in a mixture of compounds 2(a) and 2(b) which are geometric isomers. Separation of the isomers is not practicable by currently available methods. No modifications of the method of FIG. 1 can be used to prepare isolated, pure samples of 2(a) and 2(b).

Figure 2:
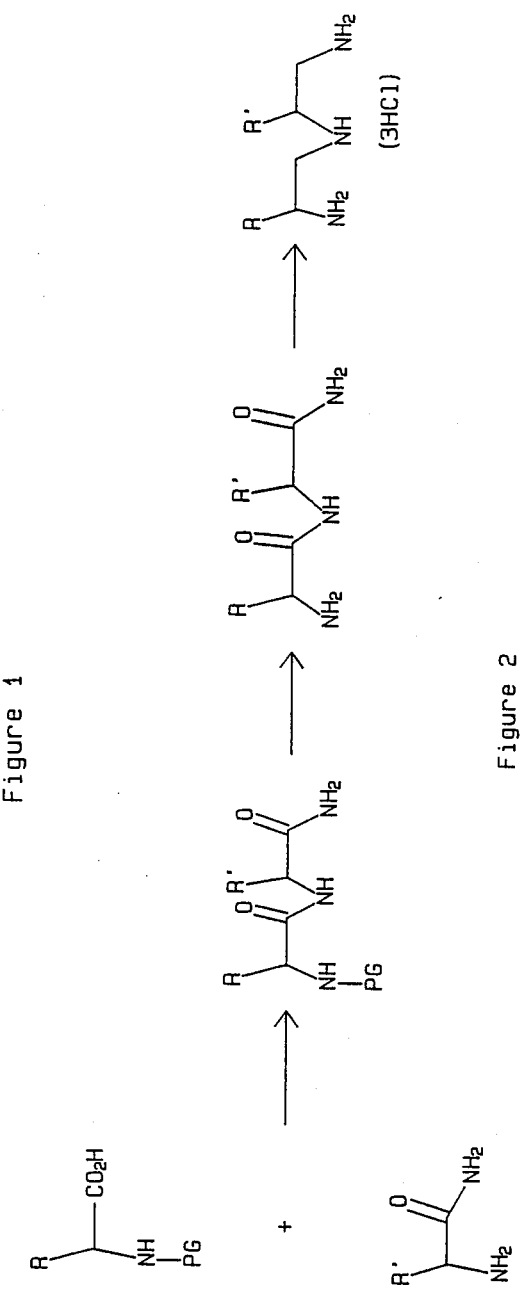
FIG. 2 shows a scheme for preparation of polysubstituted diethylenetriamine, where PG represents a protecting group (vide infra), R and R' are para-nitrobenzyl or aryl/alkyl groups, respectively, as described in the text. In the case where R is para-nitrobenzyl and R' methyl, the product diethylenetriamine is compound (a) of Table 1. In the case where R is methyl and R' is para-nitrobenzyl, the product diethylenetriamine is compound (c) of Table 1.

Since pure samples of 2(a) and 2(b) are required for pharmaceutical use, the novel processes shown in FIG. 2, 3 for preparation of the parent diethylenetriamine of the polysubstituted DTPA were devised.

According to the process of FIG. 2, to prepare compound (a), an amino-protected alpha amino acid, in this case t-butyloxycarbonyl-p-nitrophenylalanine is coupled to an amino acid amide, in this case, alanine amide, by activating the carboxylate with a suitable reagent. Such reagents are known in the art and may include inter alia the preferred 1,3-dicyclohexylcarbodiimide or other carbodiimides, carboxycarbonic esters, mixed anhydrides, and the like. The coupled product is next deprotected with trifluoroacetic acid or other deprotecting reagent, then reduced with diborane to yield the parent diethylenetriamine of 2(a). The standard alkylation, reduction and thiocarbonylation steps provide geometrically pure 2(a). Compound 3(c) can be prepared via an analogous route.

Figure 3:
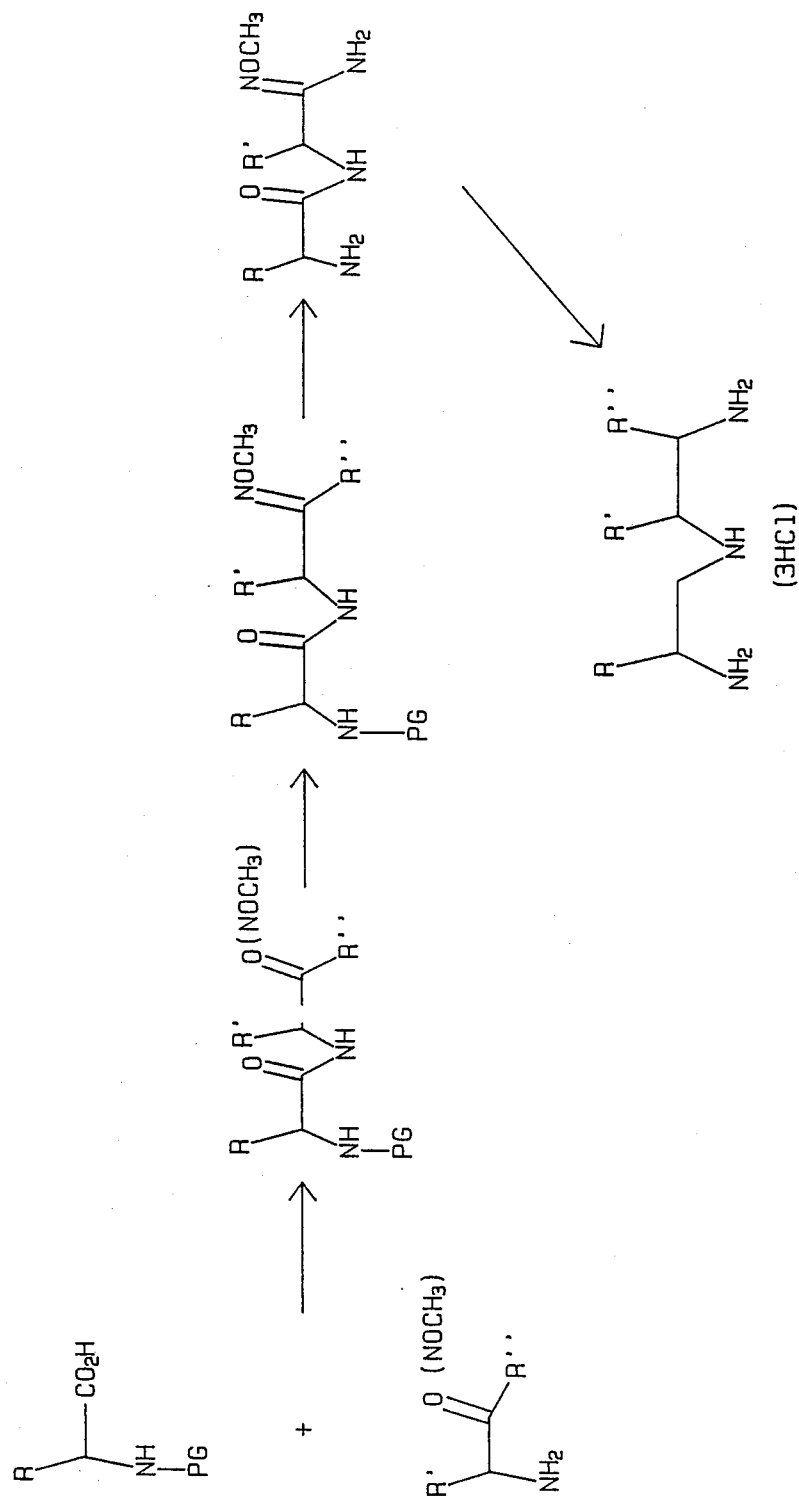
FIG. 3 shows a scheme for preparation of polysubstituted diethylenetriamine, where PG is a protecting group (vide infra), R is para-nitrobenzyl, R', R'' are alkyl/aryl groups or hydrogen, as described in the text. In the case where R' is H and R'' is methyl, the product diethylenetriamine is compound (b) of Table 1.

To prepare the parent diethylenetriamine of 2(b), the novel synthetic process of FIG. 3 was devised. According to the process shown in FIG. 3, an amino protected alpha amino acid, t-butyloxycarbonyl-p-nitrophenylalanine, is coupled to an alpha amino ketone, in this case, aminoacetone, by activating the carboxylate with a suitable reagent. Useful coupling reagents are known in the art and may include inter alia the preferred 1,3-dicyclohexylcarbodiimide or other carbodiimides, carboxycarbonic esters, mixed anhydrides or the like. Next the ketone product is converted to corresponding methyl oxime ether by reaction with methoxylamine. The resulting oxime is deprotected and reduced to provide the parent diethylenetriamine of 2(b). The standard reaction sequences of alkylation, reduction and thiocarbonylation results in geometrically pure 2(b). Of course, the reactions shown in FIG. 3 and succeeding steps can also be used to prepare compound 2(d) when 3-amino-2-butanone replaces aminoacetone. For convenience, the alpha aminoketones may be converted to their alkyl oxime ethers, preferably the methyl ether, by treatment with methoxylamine or the like, prior to coupling step in FIG. 3.

Methods for conjugating thiocyanate chelates of formulae (2) and (3) and the chelates of Table 2, are well known and described in the art (Brechbiel, et al, supra).

The choice of a protein for use in the metal chelate protein conjugate is not critical. Any desirable protein may be employed to form the conjugate. Monoclonal antibodies, of course, are often chosen as the preferred protein for the formation of metal chelate protein conjugate both for diagnostic and for therapeutic purposes. Other suitable proteins include polyclonal antibodies, antigens, blood proteins and the like. Generally, chelate and protein are mixed in a molar ratio of greater than 1:1 and less than about 100:1 depending on protein concentration. Ratios of about 2:1 to about 4:1 are preferred, but the choice of reaction conditions is within the skill of the art.

In the practice of this invention, the desired metal to be protein linked may be chelated either prior to or after linkage of the chelate to the protein. The choice of method depends on the hydrolysis tendency of the particular metal being used and is well within the ordinary skill of the art.

When a haloacetamide, a N-hydroxysuccinimide ester or an isothiocyanate is employed in the practice of this invention, that is, to form the protein conjugates, no catalyst is necessary to form the conjugate, the reaction pH of about 6 to 9.5 being desirable. The presence of a catalyst, while not necessary, may speed the conjugation reaction by a factor of 3 to 4 or more. Suitable catalysts are general base catalysts and include triethylamine, N,N-dimethylaminopyridine and the like.

Any suitable metal can be employed in the chelate including metals which exhibit paramagnetism, metals which are fluorescent and metals which are radioactive. Representative paramagnetic metals include gadolinium and iron, fluorescent metals include several metals of the lanthanide series such as terbium and europium; and radioactive metals include radionuclides of bismuth, indium, yttrium and scandium.

Metal chelation is carried out in an aqueous solution, preferably in a dilute acid medium having a pH of about 1 to about 7 and most preferably at a pH of from about 4 to about 6. Ambient temperatures of about 20° C. to 27° C. or below (to just above freezing) can be readily employed for metal chelation. Any appropriate metal salt, either in solid form or in solution, is contacted with the chelate either free in solution or protein-linked in order to form the chelated metal. The amount of metal employed may be from trace amounts to amounts in excess of equimolar with the chelate. A wide variety of metal salts may be employed including, for example, nitrates, iodides, chlorides, citrates, acetates and the like. The choice of an appropriate metal salt for any given metal as well as the choice of a particularly appriopriate chelate for any given metal is within the skill of the art. It will be apparent that the practice of this invention permits the processing of rather small quantities of metal and protein to form metal chelate and metal chelate protein conjugates.

If the preformed metal chelate is to be protein linked, the chelated metal is then mixed in aqueous solution with the desired protein at a pH of from about 6 to about 11, most preferably at a pH of from about 7 to about 9.5. Desirably, the pH is adjusted with buffered solutions such as a bicarbonate buffered solution. Once again, the choice of an appropriate buffer is within the skill of the art. The temperature of the solution can range from just above freezing to the temperature at which the chelate becomes unstable or the protein denatures. Often temperatures above 37° C. tend to denature proteins.

The metal chelate protein conjugate of this invention may be used as such with appropriate pH adjustment, if needed. Alternatively, if it is desired to purify the conjugate from unconjugated chelate or products of any side reactions, the product may be purified. A variety of standard purification techniques known in the art may be used including column chromatography and high-performance liquid chromatography (HPLC).

The invention contemplates an in vivo therapeutic procedure in which radiometal chelate conjugated monoclonal antibodies are introduced into the body and allowed to concentrate in the target region. There are a wide variety of radiometal isotopes which form stable DTPA complexes and emit cytotoxic beta particles, positrons, Auger electrons and alpha particles. Useful beta particle emitting isotopes include Sc-46, Sc-47, Sc-48, Ga-72 and Ga-73 and Y-90. Bi-212 is a useful alpha emitter. The therapeutic effect occurs when the conjugates are near or in contact with and blind to the targeted cells. Cell death may be a direct or indirect result of the radiation event of the radiometal which is positioned in close proximity to the cell.

The benefits of this aspect of the invention are several. First, the high specificity of the conjugated monoclonal antibody minimizes the total radiation dosage. Only enough radiation for the target cells need be employed. In addition, radiometal chelates generally are cleared rapidly from the body should the conjugated antibody be disrupted. The isotope can be short-lived and the affinity constant by which the isotope is retained in the chelates is very high resulting in a stably bound metal. Additionally, since the amount of radiometal employed is minimized, the radiation hazard to persons preparing and administering the radiometal chelate conjugated antibody is significantly reduced.

Because of the properties of the radiometal chelate conjugated monoclonal antibody employed by the present invention, tissue damage or whole body dose during therapy are markedly reduced as compared to that from presently employed methods of radiation therapy such as isotope implants, external radiation therapy, and immunoradiotherapy employing iodine-131 labeled polyclonal or autologous antibodies. Additionally, both biological and physical half-lives of the targeting radiobiological may now be controlled, minimizing whole body radiation effects. Since radiation is targeted to specific cell types (such as neoplastic cells) a therapeutic dose is delivered specifically to malignant cells, either localized or metastasized. The ability of radiometal chelate conjugated monoclonal antibody to provide an effective dose of therapeutic radiation specifically to metastasized cells is also unique and singularly useful for cancer therapy.

In another embodiment, the present invention contemplates an in vivo diagnostic procedure which comprises introducing a metal chelate conjugated monoclonal antibody into the body, allowing sufficient time for the conjugate to localize and identifying the degree and the site of localization, if any. The present invention also contemplates in vivo analytical procedures employing a chelate conjugated monoclonal antibody. The conjugated antibody of the present invention is substantially free of adventitiously or weakly chelated metal. The chelates conjugated to the antibody in the present invention is a derivative of diethylenetriaminepentaacetic acid (DTPA).

Other diagnostic and therapeutic techniques are described in U.S. Pat. No. 4,454,106, which is incorporated herein by reference.

The following examples are to be used for illustrative purposes only are and not to be limiting to the scope of this invention.

EXAMPLE 1

Preparation of 1,(2)-methyl-4-p-isothiocyanato benzyl)diethylenetriaminepentaacetic acid. (The mixture of geometric isomers of compounds 2(a), 2(b) in Table 1.

Methyl p-nitrophenylalanine hydrochloride

Dry methanol (200 ml) was saturated with HCl(g) in a two-necked round bottom flask cooled to $-10°$ C. p-Nitrophenylalanine (10.0 g, 47.6 mmol) was added in one portion and left to stir for about 18 hours, the solution was evaporated to near dryness on a rotary evaporator and the precipitated product collected in a Buchner funnel. After drying under vacuum at about 50° C., the yield was 10.97 grams (88.3%). A TCL (thin layer chromatography) of the free amino ester run in CHCl$_3$:MeOH (4:1) revealed an R$_f$=0.85-0.88. $^1$H NMR (220 MHz, D$_2$O, pH 1.5) 8.20 (d, 2 J=10.0), 7.53 (d, 2, J=10.0), 4.55 (t, 1, J=5.00), 3.84 (s, 3), 3.43 (m, 2); CI-MS 225 ((M+1)/z).Anal. Calcd. for C$_{10}$H$_{13}$N$_2$O$_4$Cl: C, 46.07; H, 5.03; N, 10.74; Cl, 13.60. Found: C, 45.87; H, 5.08; N, 10.48; Cl, 13.58.

N-(2-amino-[1(2)-methyl]ethyl)-p-nitrophenylalanine amide

Methyl p-nitrophenylalanine hydrochloride (9.80 g, 37.63 mmol) was treated with triethylamine (6.78 ml, 45.2 mmol) to liberate the amino ester. After removal of the solvent, the residual oil was then added dropwise in methanol (5 ml) to 1,2-diaminopropane (50 ml) at room temperature (20°-24° C.) while vigourously stirring. After stirring 18 hours, the excess solvent was removed via rotary evaporation at 50° C. at 0.01 mm of vacuum until a constant weight was achieved (10.01 g, 96%). TLC of the product in CHCl$_3$:MeOH (4:1) on silica revealed an R$_f$=0.10-0.12.
$^1$H NMR (220 MHz, D$_2$O, pH 10.0) 8.06 (d, 2, J=7.5), 7.41 (d, 2, J=7.5), 3.72 (t, 1, J=8.0), 3.18-2.73 (m,5), 0.918 (m, 3); CI-MS 267 ((M+1)/z). Anal. Calcd. for C$_{12}$H$_{18}$N$_4$O$_3$: C, 54.53; H, 6.77; N, 21.05. Found: C, 54.33; H, 6.76; N, 20.92.

1(2)-Methyl-4-(p-nitrobenzyl)diethylenetriamine trihydrochloride

N-(2-amino-[1(2)-methyl]ethyl)-p-nitrophenylalanine amide (9.90 g, 37.2 mmol) was reduced with 1M (boronhydride tetrahydrofuran) BH$_3$.THF (200 mL). A one liter three-neck round bottom flask was fitted with a reflux condenser, septum, argon inlet and bubbler exit, and flame dried. The amide (8.12 g, 38.9 mmol) was washed into the reaction flask with dry tetrahydrofuran THF (150 ml) and cooled to $-10°$ C. Next, 1M BH$_3$.THF solution (200 ml) was added with a syringe. The reaction solution was stirred one hour at $-10°$ C., then raised to a gentle reflux for 18 hours, after which it was cooled to $-10°$ C. and dry methanol (25 ml) was injected. The solution was brought to room temperature and stripped to near dryness. Methanol (25 ml) was again added and the solution evaporated to near dryness. Cleavage of the borane aggregate required a vigorous reflux of the HCl saturated ethanolic solution plus the addition of concentrated aqueous HCl (5 ml). The product precipitated cleanly and after cooling to 0° C. for 6 hours was collected and dried under vacuum (11.60 g, 86.3%). CI-MS 362 ((M+1)/z). Anal. Calcd. for C$_{12}$H$_{23}$N$_4$O$_2$Cl$_3$: C, 39.85; H, 6.65; N, 15.49. Found: C, 39.99; H, 6.64; N, 15.14.

1(2)-Methyl-4-(p-nitrobenzyl)diethylenetriaminepentaacetic acid

The parent diethylenetriamine (1.0 g, 2.77 mmol) was treated with bromoacetic acid (5.767 g, 41.5 mmol) and 7N KOH (13.04 ml). The reaction solution was allowed to stir for 72 hours at room temperature. The solution was acidified to pH 1.5 with concentrated HBr and extracted with ether (3×100 ml). The aqueous solution was evaporated to a solid and loaded onto a 2.6×30 cm ion exchange column AG50W×8, 200-400 mesh, H+ form, (BioRad Inc., Richmond CA) and washed with H$_2$O to removed the unreacted materials, hydrolysis products and salts. The crude product was eluted with 2N aqueous NH$_3$. The crude product was further purified by HPLC using a 10×250 mm, C$_{18}$ reverse phase column with a 25 minute gradient of aqueous 0.05M triethylammonium acetate to 100% methanol at a flow rate of 3 ml/min. The product had a retention time of 9.1 minutes. The combined fractions from the HPLC were re-chromatographed on an AG50W×8 column as specific above to remove the triethylammonium acetate buffer. The product was collected and the solvent evaporated to a solid (0.648 g, 43.2%).

1(2)-Methyl-4-(p-aminobenzyl)diethylenetriaminepentaacetic acid

The parent nitrobenzyl DTPA (100.0 mg, 0.1845 mmol) was hydrogenated with Pd/C. A water-jacketed three-neck flask (50 ml) was charged with 10% Pd/C (43 mg), H₂O (5 ml) and a stirring bar. The center neck was attached to an atmospheric hydrogenation apparatus, one side neck was fitted with an injection valve, and the remaining neck was firmly stoppered. The assembled hydrogenation apparatus was evacuated and flushed with hydrogen while the reaction flask was cooled to 4° C. The nitrocompound was dissolved in H₂O (10 ml) and 5M NaOH was added to bring the pH to 10.0 The solution was injected into the reaction flask and hydrogen uptake monitored. After the reaction, the mixture was filtered through a fine frit with Celite 535 (Fluka AG, Switzerland). The solvent was removed and the residue dried under vacuum for 18 hours with yield being essentially quantitative.

1(2)-Methyl-4-(p-isothiocyanatobenzyl)diethylenetriaminepentaacetic acid (The mixture of compounds, a, b in Table 2.)

The parent mixture of aniline precursors to compound 2(a), 2(b) and described above (0.095 g, 0.1845 mmol) was dissolved in H₂O (5 ml) pH 8.5 and converted to a crude product by treatment with thiophosgene (0.212 g, 1.845 mmol) in CHCl₃ (10 ml). The crude product was purified by column chromatography on a 1×30 cm Florisil (Sigma, St. Louis, Mo.) column eluted with CH₃CN:H₂O (30:8) with the product eluting first. The solvent was removed with minimum heating and the remaining aqueous solution lyophilized overnight. The $R_f$ of the product on silica using CH₃CN:H₂O (30:8) was 0.20. The IR spectrum possessed the characteristic absorption at 2100 cm$^{-1}$ for the isothiocyanate.

EXAMPLE 2

Compound 2(d) of Table 2 is prepared by the method of example 1 by simply substituting 2,3-diaminobutane for 1,2-diaminopropane in the second step of the synthesis.

EXAMPLE 3

Preparation of 1-p-isothiocyantobenzyl)-3-methyl DTPA. (Synthesis of compound 2(a) in Table 1 as a single geometric isomer).

t-Butoxycarbonyl-(d,1)-p-nitrophenylalanine p-Nitrophenylalanine (7.94 g, 37.8 mmol) was dissolved in 50% aqueous dioxane solution (60 ml) and triethylamine (7.9 ml, 56.7 mmol) added [2-(t-butoxycarbonyloxyamino)2-phenylacetonitrile]. (10.24 g, 41.6 mmol, Aldrich Chemical Co.) was added and the solution stirred for two hours. Ethyl acetate (100 ml) and H₂O (50 ml) were added and the contents poured into a separatory funnel. The aqueous layer was retained and extracted twice with ethyl acetate (100 ml). The aqueous layer was cooled to 0° C. and the pH was adjusted to 2.0 with 3NHCl, whereupon a precipitate formed which was collected and dried under vacuum. The filtrate was extracted with ethyl acetate twice (100 ml), dried over MgSO₄ and stripped to dryness. The two fractions proved to be identical and were combined (11.0 g, 94.0%). The melting point of the compound was 165° C.

¹H NMR (220 MHz, DMSO-d₆) 8.036 (d, 2, J=8.00), 7.29 (d, 2, J=8.00), 5.38 (d, 1, J=8.00), 4.44 (m, 1), 3.25 (dd, 1, J=13.0, 6.00), 3.05 (dd, 1, J=13.0, 6.0), 1.39 (s, 9); CI-MS 311 ((M+1)/z).

t-Butoxycarbonyl-(d1)-p-nitrophenylalaninyl-(1)-alanine amide

BOC-(d1)-p-nitrophenylalanine (10.0 g, 32.26 mmol), 1-alanine amide hydrobromide (5.45 g, 32.26 mmol), triethylamine (4.487 ml, 32.36 mmol), and 1-hydroxybenzotriazole (3.84 g, 28.4 mmol) were dissolved in ethyl acetate (400 ml). Dicyclohexylcarbodiimide (7.30 g, 35.44 mmol) in ethyl acetate (25 ml) was added and the reaction mixture was allowed to stir for 18 hours after which three drops (about 0.15 ml) of concentrated acetic acid were added. The dicyclohexylurea was filtered off and the filtrate was extracted sequentially with saturated sodium chloride salt solution (100 ml), 1N HCl (3×100 ml), saturated salt solution (100 ml), 5% NaHCO₃ (3×100 ml), and saturated salt solution (100 ml). The organic solution was dried over MgSO₄, filtered, and reduced to 50 ml. Petroleum ether (50 ml) was added and the contents of the flask were cooled to 0° C. for 12 hours. The precipitate was collected on a Buchner funnel and dried under vacuum (10.55 g, 86.1%).

¹H NMR (220 MHz, CDCl₃/d₆-DMSO) 8.08 (d, 2, J=9.0), 7.91 (m, 1), 7.45 (d, 2, J=9.0), 7.14 (d, 1, J=12.0), 6.68 (m, 2), 4.35 (m, 2), 3.17 (dd, 1, J=15.06, 6.0), 2.98 (dd, 1. J=15.0, 8.0), 1.38 (s, 9); CI-MS 381 ((M+1)/z).

Anal. Calcd. for C₁₇H₂₄N₄O₆: C, 53.68; H, 6.31; N, 14.73. Found: C, 53.92; H, 6.59; N, 14.84.

2-Methyl-4-(p-nitrobenzyl)diethylenetriamine trihydrochloride

The dipeptide amide described above (5.10 g, 13.42 mmol) was deprotected by treatment with trifluoroacetic acid (50 ml) for one hour after which the solution was rotary evaporated to near dryness. Methanol (50 ml) was added and the solution was taken to dryness. The resulting solid was held at 0.01 mm and 50° C. for 8 hours to insure removal of the residual acid.

The resulting ammonium salt (5.10 g, 13.42 mmol) in THF (50 ml) was added to a flame dried 250 ml three neck flask fitted with a condenser under argon atmosphere. The flask was cooled to 0° C. and 1M BH₃.THF (30.8 ml) was added via syringe. The reaction solution was heated to a vigorous reflux for two hours and then allowed to stir at room temperature for an additional two hours. The reaction flask was cooled to 0° C. and methanol (25 ml) was slowly injected to decompose excess hydride. The solution was reduced to dryness, taken up in absolute ethanol (50 ml), and concentrated HCl (50 ml) was added. The solution was vigorously refluxed for two hours and then stripped to dryness. The residue was dissolved in H₂O, loaded onto a 1.5×20 cm AG50W8, H+ form, ion exchange column, and washed with H₂O until the eluant was neutral. The product was eluted from the column with concentrated HCl (125 ml), concentrated to 10 ml, and lyophilized overnight. The remaining solid was found to be substantially pure (1.823 g, 66.2%).

¹H NMR (500 MHz, D₂O, pH 1.0) 8.268 (d, 2, J=8.0), 7.614 (d, 2, J=8.0), 4.106 (m, 1), 3.773 (m, 1), 3.680–3.450 (m, 3), 3.393 (m, 1), 3.312 (m, 1), 3.212 (m, 1), 1.493 (br. t, 3); (500 MHz, D₂O, pH 11.0) 8.091 (d, 2, J=8.0), 7.438 (d, 2, J=8.0), 3.167 (m, 1), 2.910 (m, 1), 2.75–2.45 (overly complicated multiplet, 6), 1.031 (br. s, 3); CI-MS 253 ((M+1)/z). Anal. Calcd. for C₁₂H₂₃N₄O₂Cl₃: C, 39.85; H, 6.36; N, 15.49. Found: C, 39.88; H, 6.36; N, 15.28.

Conversion of this diethylenetriamine to compound 2(a) was achieved by the method described in Example 1.

EXAMPLE 4

Preparation of 1-p-isothiocyanatobenzyl-4-methyl DTPA (compound 2(b) prepared as a pure geometric isomer following the scheme shown in FIG. 3).

BOC-p-nitrophenylalanine 2-oxopropyl amide t-Butyloxycarbonyl-p-nitrophenylalanine (4.42 g, 14.26 mmol, aminoacetone hydrochloride (1.56 g, 14.26 mmol), triethylamine (1.44 g, 14.26 mmol), 1-hydroxybenzotriazole (1.69 g, 12.55 mmol), were dissolved in ethyl acetate (400 ml). 1,3-Dicyclohexylcarbodiimide (3.23 g, 15.68 mmol) in ethyl acetate (25 ml) was added and the solution allowed to stir for 18 hours. Glacial acetic acid (0.2 ml) was added and the solution was filtered. The filtrate was extracted with saturated salt solution (100 ml), 1N HCl solution (3×100 ml), saturated salt solution (100 ml), 5% bicarbonate solution (3×100 ml), and saturated salt solution (100 ml). The organic phase was dried over $MgSO_4$, filtered and concentrated to 50 ml. Petroleum ether (50 ml) was added and the solution was cooled to 0° C. for 12 hours. The precipitated product was collected and dried under vacuum.

BOC-p-nitrophenylalanine-2-(oxime methyl ether)propyl amide

The ketone (2.00 g, 5.47 mmol) was dissolved in pyridine (10 ml) and methoxylamine hydrochloride (0.914 g, 10.95 mmol) was added. The solution was allowed to stir for 12 hours after which the solvent was removed. The residue was dissolved in minimal ethyl acette and crystallized by addition of petroleum ether to yield the oxime ether amide.

1-Methyl-4-(p-nitrobenzyl)diethylenetriamine trihydrochoride

The oxime ether (3.00 g, 7.61 mmol) was deprotected by stirring with neat trifluoroacetic acid (10 ml). The solvent was removed by high vacuum rotary evaporation.

The residue was dissolved in tetrahydrofuran (50 ml) and added to a flame dried flask fitted with a reflux condenser, an argon inlet and bubbler exit, and an injection port. The solution was cooled to 0° C. and 1M $BH_3.THF$ (200 ml) was added via syringe. The reaction was refluxed for 6 hours, cooled to 0° C., and methanol (25 ml) was added decomposing any excess hydride. The solution was rotary evaporated to near dryness and the residue was taken up in ethanol (100 ml). The ethanol solution was saturated with HCl(g) and refluxed for four hours, after which the solution was cooled for 18 hours at 0° C. The precipitate was collected, washed with diethyl ether, and dried under vacuum.

Conversion of this diethylenetriamine to compound 2(b) was achieved by the method described in Example 1.

EXAMPLE 5

A monoclonal antibody specific for the Rauscher leukemia virus was labeled with a mixture of the chelates a and b of Table 2 as follows. The antibody was suspended in a buffered normal saline solution having a pH of about 8.5. The chelates were added in aqueous solution. This protein solution after reaction overnight was purified by dialysis against metal free 0.05 M citrate, 0.15 M NaCl buffer, pH 5.5. Before labeling with metal, the protein was dialysed against a solution comprising 0.02 M N-morpholinoethanesulfonic acid and 0.08 M in acetate, pH 5.9. To label with Yttrium-90, the protein solution was reacted with an acetate solution of the isotope at pH ranging about 4 to 5.5 and purified by passage through a TSK 3000 size exclusion column (Beckman Inc., Berkley, CA) and by dialysis. When the labeled antibody thus prepared was injected into mice bearing spleens invaded with the Rauscher leukemia virus, the antibody was seen to localize in the spleen with about 30% of injected dose bound to the tumorous spleen and only 1-2% of the radioactive dose was found in the bone, where it would destroy bone marrow. In contrast, antibody labeled by using the mixed anhydride of DTPA of prior art, when labelled with Y-90 as above and injected into the same mouse tumor model, also localized in the spleen to about the same degree but with about 8-12% of injected radioactive dose being undesirably found in bone marrow (data not shown).

In a separate study, antibody was labeled with Bismuth-212 or Bi-206 by reaction of iodide solutions of the isotopes with the antibody prepared with chelates 2a, 2b as described in Table 2. These preparations were also injected into mice and tissue distribution data showed that 5-10% of the dose was found in kidney, the natural repository of unchelated bismuth. However, antibody labeled by use of the mixed anhydride chelate of prior art lose as much as 50% of the dose to kidney during the same time causing kidney damage. Labelling with other radioactive isotopes is similarly done and tests on the target tissue or organ similarly performed.

These studies demonstrate the remarkable utility of the chelates of the present invention for use in specifically transporting therapeutic isotopes to tumors while minimizing the distribution of the compounds to non-targeted organs such as kidney and bones. Imaging of the target tissue or organ can, of course, be done by standard radiographic techniques well known in the art.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. Polysubstituted diethylenetriaminepentaacetic acid (DTPA) chelating agent of the following formula 1 or 2 having one side chain attached to the carbon backbone of the DTPA, said side chain being an alkyl-aryl group with n=1-5, and which contains a functional moiety X selected from the group consisting of nitro, N-hydroxysuccininimide ester, N-hydroxysuccininimide isothiocyanate and haloacetamide groups, and which has one or more additional side chains ($R_1$-$R_4$) and ($R'_1$-$R'_4$) linked to the carbon backbone of the DTPA, said ($R_1$-$R_4$) and ($R'_1$-$R'_4$) being selected from the group consisting of hydrogen, straight or branched chain alkyl group with 1-15 carbon atoms, aryl group with 1-15 carbon atoms, and mixture thereof, wherein at least one of the additional side chains must contain at least one carbon atom:

FORMULA 1

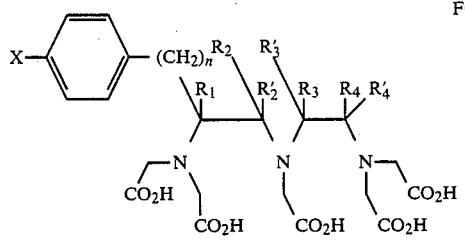

FORMULA 2

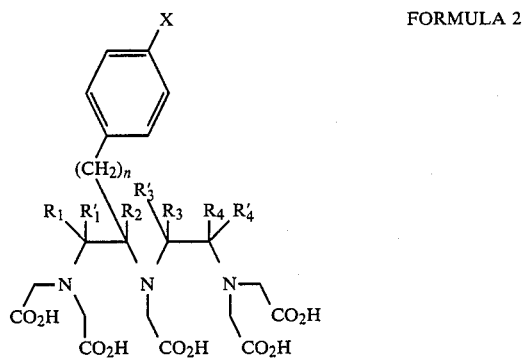

2. The polysubstituted diethylenetriminepentaacetic acid chelating agent of claim 15 in which X is a N-hydroxysuccininimide ester group.

3. The polysubstituted DTPA chelating agent of claim 1, having the following formula 3 or 4:

FORMULA 3

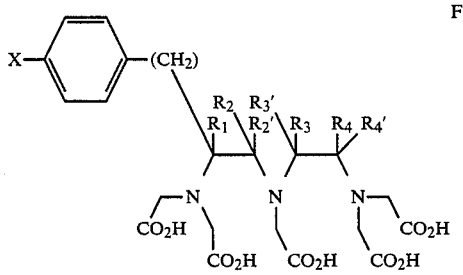

FORMULA 4

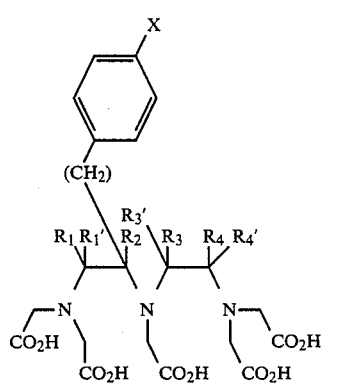

wherein X is nitro, amino or isothiocyanate group; and wherein ($R_1$–$R_4$) and ($R'_1$–$R'_4$) groups are as follows:

| Formula | $R_1, R_1'$ | $R_2, R_2'$ | $R_3, R_3'$ | $R_4, R_4'$ |
|---|---|---|---|---|
| 3 | H | H, H | $CH_3$, H | H, H |
| 3 | H | H, H | H, H | $CH_3$, H |
| 3 | H | H, H | $CH_3$, H | $CH_3$, H |
| 4 | H, H | H | $CH_3$, H | H, H |
| 4 | H, H | H | H, H | $CH_3$, H |

-continued

| Formula | $R_1, R_1'$ | $R_2, R_2'$ | $R_3, R_3'$ | $R_4, R_4'$ |
|---|---|---|---|---|
| 4 | H, H | H | $CH_3$, H | $CH_3$, H |

4. A chelating agent selected from the group consisting of:
2-(para-nitrobenzyl)diethylenetriaminepentaacetic acid,
2-(para-aminobenzyl)diethylenetriaminepentaacetic acid, and
2-(para-isothiocyanatobenzyl)diethylenetriaminepentaacetic acid.

5. A method for preparing polysubstituted diethylenetriaminepentaacetic acid chelating agent of the following formula 1 or 2:

FORMULA 1

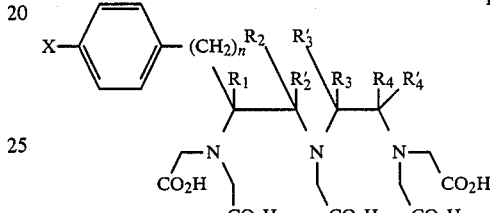

FORMULA 2

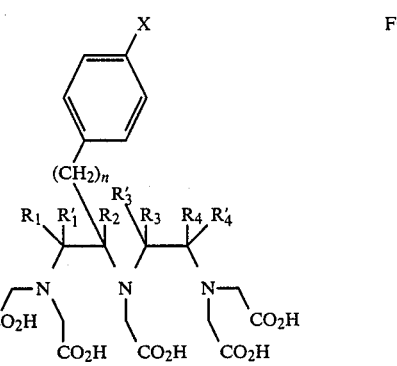

where the substituents ($R_1$–$R_4$) and ($R'_1$–$R'_4$) are selected from the group consisting of hydrogen, straight or branched chain alkyl group with 1–15 carbon atoms, aryl group with 1–15 carbon atoms, and mixture thereof, wherein X is hydrogen, alkyl group of 1–15 carbon atoms, alkyl-aryl group of 1–15 carbons atoms, nitro, methoxy or hydroxy and wherein N=1–5, the method comprising the sequential steps of:

(a) reacting an amino protected alpha amino acid of the following formula 3:

FORMULA 3

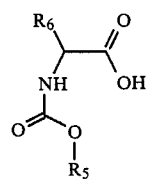

wherein the protecting group $R_5$ is tertiary butyl (BOC), benzyl (CBZ), or 9-fluorenylmethyl (Fmoc) and $R_6$ is selected from said ($R_1$–$R_4$) and ($R'_1$–$R'_4$) groups with an alpha amino acid amide of the following fomula 4:

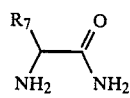

FORMULA 4 where $R_7$ is selected from said ($R_1$-$R_4$) and ($R'_1$-$R'_4$) groups to produce a coupled diamide;

(b) then deprotecting said diamide prior to reduction by reducing agent to produce a diethylenetriamine substituted with selected substituents; and (c) then converting said diethylene triamine substituted with selected substituents to polysubstituted diethylenetriaminepentaacetic acid of formula 1 or 2 by an alkylation reaction with haloacetic acid.

6. A method for preparing an ester of polysubstituted diethylenetriaminepentaacetic acid chelating agent, comprising reacting a haloacetate ester with the diethylenetriamine of claim 5.

7. A method for preparing polysubstituted diethylenetriaminepentaacetic acid chelating agent of formula 1, 2:

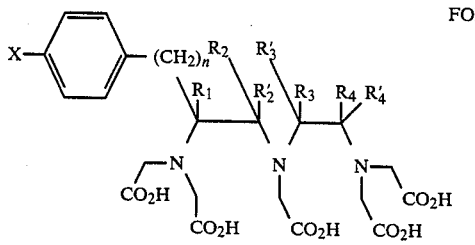

FORMULA 1

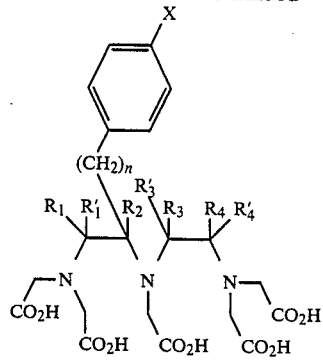

FORMULA 2 where the substituents ($R_1$-$R_4$) and ($R'_1$-$R'_4$) are selected from the group consisting of hydrogen, straight or branched chain, alkyl group with 1-15 carbon atoms, aryl group with 1-15 carbon atoms, and mixture thereof, wherein X is hydrogen, alkyl group of 1-15 carbon atoms, alkyl-aryl group of 1-15 carbons atoms, nitro, methoxy or hydroxy and wherein N=1-5, the method comprising the sequential steps of:

(a) reacting an amino protected alpha amino acid of the following formula 5:

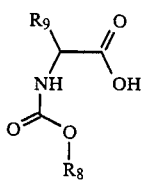

FORMULA 5 where, in the protecting group, $R_8$ is tertiary butyl (BOC), benzyl (CBZ), or 9-fluorenylmethyl (Fmoc) and $R_9$ is selected from said ($R_1$-$R_4$) and ($R'_1$-$R'_4$) with an alpha amino ketone of formula 6:

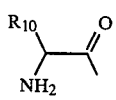

FORMULA 6 where $R_{10}$ is selected from said ($R_1$-$R_4$) and ($R'_1$-$R'_4$) groups to produce the resulting keto amide;

(b) then converting said keto amide to an oxime ether amide by reaction with methoxylamine;

(c) then deprotecting said amide, prior to reduction, by a reducing agent to produce a diethylenetriamine subsituted with the selected substitutents; and (d) then converting said diethylene triamine substituted with selected substituents to polysubstituted diethylenetriaminepentaacetic acid of formula 1 or 2 an alkylation reaction with haloacetic acid.

8. A method for preparing esters of polysubstituted diethylenetriaminepentaacetic acid (DTPA) chelating agent comprising reacting any suitable haloacetic acid ester with the diethylenetriamine of claim 7.

* * * * *